(12) United States Patent
Huey et al.

(10) Patent No.: US 8,252,318 B2
(45) Date of Patent: Aug. 28, 2012

(54) DEVICES AND METHODS FOR THE DELIVERY OF BLOOD CLOTTING MATERIALS TO BLEEDING WOUNDS

(75) Inventors: Raymond J. Huey, Orange, CT (US); Jeffrey L. Horn, Rocky Hill, CT (US)

(73) Assignee: Z-Medica Corporation, Wallingford, CT (US)

( * ) Notice: Subject to any disclaimer, the term of this patent is extended or adjusted under 35 U.S.C. 154(b) by 759 days.

(21) Appl. No.: 11/592,477

(22) Filed: Nov. 2, 2006

(65) Prior Publication Data

US 2007/0065491 A1  Mar. 22, 2007

Related U.S. Application Data

(63) Continuation-in-part of application No. 11/054,918, filed on Feb. 9, 2005.

(51) Int. Cl.
*A61L 15/14* (2006.01)
*A61L 15/16* (2006.01)
*A61L 15/18* (2006.01)
*A61K 9/14* (2006.01)
*A61F 13/00* (2006.01)

(52) U.S. Cl. ........ 424/445; 424/444; 424/489; 424/446; 424/447; 602/42; 602/43; 602/45; 602/46; 602/53; 502/80

(58) Field of Classification Search .............. 424/445, 424/444, 489, 446, 447; 602/42, 43, 45, 602/46, 53, 57; 502/80
See application file for complete search history.

(56) References Cited

U.S. PATENT DOCUMENTS

| | | |
|---|---|---|
| 3,122,140 A | 2/1964 | Crowe et al. |
| 3,181,231 A | 5/1965 | Breck |
| 3,366,578 A | 1/1968 | Michalko |
| 3,979,335 A | 9/1976 | Golovko et al. |
| 4,373,519 A | 2/1983 | Errede et al. |

(Continued)

FOREIGN PATENT DOCUMENTS

EP  0296324  12/1988

(Continued)

OTHER PUBLICATIONS

Donald Voet & Judith Voet, "Molecular Physiology", Biochemistry, p. 1087-1096, vol. 64, 1990, John Wiley & Sons.

(Continued)

*Primary Examiner* — Savitha Rao
(74) *Attorney, Agent, or Firm* — Knobbe Martens Olson & Bear, LLP (57) ABSTRACT

An apparatus for promoting the clotting of blood and controlling bleeding comprises a receptacle for retaining blood clotting material in particulate form therein. A pad for controlling bleeding comprises a mesh structure and a support attached to the mesh structure to facilitate the application of pressure to the pad and the wound. A bandage applicable to a bleeding wound comprises a mesh structure and a flexible substrate attached to the mesh structure, the substrate being a cloth or plastic member that may be adhesively attachable to cover a wound. In any embodiment, at least a portion of the receptacle or mesh structure is defined by a mesh having openings therein, and at least a portion of the particulate blood clotting material is in direct contact with blood. The mesh may include a zeolite powder impregnated or otherwise incorporated therein.

20 Claims, 4 Drawing Sheets

U.S. PATENT DOCUMENTS

| | | | |
|---|---|---|---|
| 4,514,510 | A | 4/1985 | Alexander |
| 4,525,410 | A | 6/1985 | Hagiwara et al. |
| 4,626,550 | A | 12/1986 | Hertzenberg |
| 4,748,978 | A | 6/1988 | Kamp |
| 4,822,349 | A | 4/1989 | Hursey et al. |
| 4,911,898 | A | 3/1990 | Hagiwara et al. |
| 4,938,958 | A | 7/1990 | Niira et al. |
| 4,956,350 | A | 9/1990 | Mosbey |
| 5,474,545 | A | 12/1995 | Chikazawa |
| 5,538,500 | A | 7/1996 | Peterson |
| 5,556,699 | A | 9/1996 | Niira et al. |
| 5,696,101 | A * | 12/1997 | Wu et al. ........................ 514/57 |
| 5,716,337 | A | 2/1998 | McCabe et al. |
| 5,801,116 | A | 9/1998 | Cottrell et al. |
| 5,964,349 | A | 10/1999 | Odagiri |
| 5,981,052 | A | 11/1999 | Sugiyama |
| 6,037,280 | A | 3/2000 | Edwards et al. |
| 6,060,461 | A | 5/2000 | Drake |
| 6,123,925 | A | 9/2000 | Barry et al. |
| 6,159,232 | A | 12/2000 | Nowakowski |
| 6,187,347 | B1 | 2/2001 | Patterson et al. |
| 6,428,800 | B2 | 8/2002 | Greenspan et al. |
| 6,495,367 | B1 | 12/2002 | Isogawa et al. |
| 6,998,510 | B2 | 2/2006 | Buckman et al. |
| 7,371,403 | B2 | 5/2008 | McCarthy et al. |
| 2002/0197302 | A1 | 12/2002 | Cochrum et al. |
| 2003/0133990 | A1* | 7/2003 | Hursey et al. ................ 424/601 |
| 2003/0176828 | A1 | 9/2003 | Buckman et al. |
| 2003/0208150 | A1 | 11/2003 | Bruder et al. |
| 2004/0166172 | A1 | 8/2004 | Rosati et al. |
| 2005/0074505 | A1* | 4/2005 | Hursey ........................ 424/682 |
| 2005/0118230 | A1 | 6/2005 | Hill et al. |
| 2006/0078628 | A1 | 4/2006 | Koman et al. |
| 2006/0141018 | A1 | 6/2006 | Cochrum et al. |
| 2006/0172000 | A1 | 8/2006 | Cullen et al. |
| 2007/0154510 | A1 | 7/2007 | Wilcher et al. |
| 2007/0275073 | A1 | 11/2007 | Huey et al. |
| 2008/0146984 | A1 | 6/2008 | Campbell et al. |
| 2008/0199539 | A1 | 8/2008 | Baker et al. |
| 2008/0319476 | A1 | 12/2008 | Ward et al. |

FOREIGN PATENT DOCUMENTS

| | | |
|---|---|---|
| EP | 0 888 783 A1 | 7/1999 |
| EP | 1159972 A2 * | 12/2001 |
| EP | 1690553 A1 | 8/2006 |
| EP | 1810697 A2 | 7/2007 |
| GB | 2314842 A * | 1/1998 |
| JP | 11-332909 A1 | 7/1999 |
| WO | WO 95/05445 | 2/1995 |
| WO | WO 01/82896 A1 | 8/2001 |
| WO | WO 02/30479 A1 | 4/2002 |
| WO | WO 02/060367 A1 | 8/2002 |
| WO | WO 02/074325 A1 | 9/2002 |
| WO | WO 2005/027808 A1 | 3/2005 |
| WO | WO 2006/012218 A1 | 2/2006 |
| WO | WO 2006/088912 A2 | 8/2006 |
| WO | WO 2007/120342 A2 | 10/2007 |
| WO | WO 2008/036225 A2 | 3/2008 |

OTHER PUBLICATIONS

European Search Report for Applilcation No. 05445078 dated Jun. 27, 2006.
The Merck Index; 1989, pp. 1596-1597, abstract 10021.
Co-pending U.S. Appl. No. 10/939,687, filed Sep. 13, 2004.
Co-pending U.S. Appl. No. 10/939,869, filed Sep. 13, 2004.
Co-pending U.S. Appl. No. 11/023,869, filed Dec. 27, 2004.
Co-pending U.S. Appl. No. 11/054,918, filed Feb. 9, 2005.
Co-pending U.S. Appl. No. 11/082,716, filed Mar. 16, 2005.
Co-pending U.S. Appl. No. 11/303,607, filed Dec. 16, 2005.
Co-pending U.S. Appl. No. 11/404,126, filed Apr. 13, 2006.
Co-pending U.S. Appl. No. 11/544,238, filed Oct. 6, 2006.
Co-pending U.S. Appl. No. 11/584,079, filed Oct. 20, 2006.
Co-pending U.S. Appl. No. 11/586,986, filed Oct. 25, 2006.
Co-pending U.S. Appl. No. 11/590,427, filed Oct. 30, 2006.
Co-pending U.S. Appl. No. 11/606,617, filed Nov. 29, 2006.
Co-pending U.S. Appl. No. 11/633,687, filed Dec. 4, 2006.
Co-pending U.S. Appl. No. 11/634,673, filed Dec. 5, 2006.
Co-pending U.S. Appl. No. 11/634,531, filed Dec. 6, 2006.
Co-pending U.S. Appl. No. 11/654,409, filed Jan. 17, 2007.
Co-pending U.S. Appl. No. 11/710,106, filed Feb. 22, 2007.
Co-pending U.S. Appl. No. 11/715,057, filed Mar. 6, 2007.
Co-pending U.S. Appl. No. 12/101,336, filed Apr. 11, 2008.
Co-pending U.S. Appl. No. 12/101,346, filed Apr. 11, 2008.
Co-pending U.S. Appl. No. 12/140,356, filed Jun. 17, 2008.
Co-pending U.S. Appl. No. 12/204,129, filed Sep. 4, 2008.
U.S. Appl. No. 60/668,022, filed Apr. 4, 2005.
U.S. Appl. No. 60/708,206, filed Aug. 15, 2005.
U.S. Appl. No. 60/902,738, filed Feb. 21, 2007.
U.S. Appl. No. 60/955,854, filed Aug. 14, 2007.
Office Action for U.S. Appl. No. 11/398,161 dated Apr. 30, 2008.
U.S. Appl. No. 12/352,513, filed Jan. 12, 2009.
U.S. Appl. No. 10/939,687, filed Sep. 13, 2004 including prosecution history, including but not limited to Non-Final Rejection dated Oct. 16, 2006, Final Rejection dated May 24, 2007, Non-Final Rejection dated Sep. 6, 2007, Final Rejection dated Nov. 28, 2007 and Examiner's Answer to Appeal Brief.
U.S. Appl. No. 10/939,869, filed Sep. 13, 2004 including prosecution history, including but not limited to Non-Final Rejection dated Feb. 8, 2008, Non-Final Rejection dated Sep. 17, 2008 and Final Rejection dated Apr. 17, 2009.
U.S. Appl. No. 11/023,869, filed Dec. 27, 2004 including prosecution history, including but not limited to Requirement for Restriction/Election dated Mar. 31, 2008, Non-Final Rejection dated May 12, 2008 and Non-Final Rejection dated Dec. 11, 2008.
U.S. Appl. No. 11/054,918, filed Feb. 9, 2005 including prosecution history, including but not limited to Non-Final Office Rejection dated Mar. 18, 2008, Final Rejection dated Sep. 16, 2008 and Non-Final Rejection dated Mar. 9, 2009.
U.S. Appl. No. 11/082,716, filed Mar. 16, 2005 including prosecution history, including but not limited to Non-Final Rejection dated Oct. 9, 2008.
U.S. Appl. No. 11/303,607, filed Dec. 16, 2005 including prosecution history, including but not limited to Requirement for Restriction/Election dated Feb. 21, 2008, Non-Final Rejection dated Apr. 29, 2008 and Non-Final Rejection dated Sep. 8, 2008.
U.S. Appl. No. 11/404,126, filed Apr. 13, 2006 including prosecution history, including but not limited to Requirement for Restriction/Election dated Sep. 16, 2008 and Non-Final Rejection dated Dec. 3, 2008.
U.S. Appl. No. 11/544,238, filed Oct. 6, 2006 including prosecution history, including but not limited to Requirement for Restriction/Election dated Dec. 11, 2008; Non-Final Office Action dated May 29, 2009.
U.S. Appl. No. 11/584,079, filed Oct. 20, 2006 including prosecution history, including but not limited to Non-Final Rejection dated Apr. 6, 2009.
U.S. Appl. No. 11/590,427, filed Oct. 30, 2006 including prosecution history, including but not limited to Non-Final Rejection dated Aug. 19, 2008 and Final Rejection dated May 26, 2009.
U.S. Appl. No. 11/633,687, filed Dec. 4, 2006 including prosecution history, including but not limited to Requirement for Restriction/Election dated Jun. 25, 2008; Non-Final Rejection dated Sep. 4, 2998 and Final Office Action dated Jun. 1, 2009.
U.S. Appl. No. 11/634,673, filed Dec. 5, 2006 including prosecution history, including but not limited to Requirement for Restriction/Election dated Apr. 9, 2008, Non-Final Rejection dated May 12, 2008, Final Rejection dated Nov. 14, 2008 and Non-Final Rejection dated May 21, 2009.
U.S. Appl. No. 11/715,057, filed Mar. 6, 2007 including prosecution history, including but not limited to Non-Final Rejection dated Aug. 20, 2008 and Final Rejection dated Apr. 2, 2009.
Alam, et al., Application of a Zeolite Hemostatic Agent Achieves 100% Survival in a Lethal Model of Complex Groin Injury in Swine, May 2004, The Journal of Trauma Injury, Infection, and Critical Care, vol. 56, pp. 974-983.
European Search Report for Application No. 05445078 dated Jun. 27, 2006.

Supplementary Partial European Search Report for Application No. EP04783867 dated Jan. 29, 2008.
International Search Report for Application No. PCT/US2004/029812, dated Jun. 14, 2005.
International Search Report for Application No. PCT/US2006/004594, dated Nov. 3, 2006.
International Search Report for Application No. PCT/US2006/012487, dated Dec. 12, 2006.
International Search Report for Application No. PCT/US2007/016509, dated Feb. 8, 2008.
International Search Report for Application No. PCT/US2008/075191, dated Nov. 17, 2008.
PCT Search Report for PCT/US2004/029809, dated Feb. 24, 2005.
PCT International Preliminary Report for PCT/US2007/016509, dated May 14, 2009.
PCT Search Report for PCT/US2005/046700, dated Jul. 6, 2006.
Search Report for EP 05020602, dated Jul. 6, 2006.
Search Report for EP 06126082, dated May 11, 2007.
Search Report for EP 06123557, dated Feb. 29, 2008.
IMA-EU, Kaolin, Oct. 2006, p. 1-2.
The Merck Index; 1989, pp. 1596-1597, abstract 10021. Donald Voet & Judith Voet, "Molecular Physiology", Biochemistry, p. 1087-1096, vol. 64, 1990, John Wiley & Sons.
Le Van Mao, Raymond et al. "Mesporous Aluminosilicates prepared from Zeolites by Treatment with Ammonium Fluorosilicate." J. Mater. Chem. 1993. pp. 679-683. vol. 3, No. 6.

Dyer, A. et al. "Diffusion in heteroionic zeolites: part 1. Diffusion of water in heteroionics natrolites." Microporous and Mesoporous Materials. 1998. pp. 27-38. vol. 21.
Gielen, M., Solid State Organometallic Chemistry: Methods and Applications Physical Organometallic Chemistry, 1999, New York John Wiley & Sons, Ltd. (UK), V. 2, p. 156.
Hursey, et al., Bandage Using Molecular Sieves, Apr. 18, 2002, International Application Published Under the PCT, WO 02/30479 A1.
Alam, et al., Comparative Analysis of Hemostatic Agents in a Swine Model of Lethal Groin Injury, Jun. 2003, The Journal of Trauma Injury, Infection, and Critical Care, vol. 54, No. 6, pp. 1077-1082.
Wright, J.K. et al. "Thermal Injury Resulting from Application of a Granular Mineral Hemostatic Agent." The Journal of Trauma Injury, Infection, and Critical Care. 2004. pp. 224-230. vol. 57, No. 2.
Top, Ayben et al. "Silver, zinc, and copper exchange in a Na-clinoptilolite and resulting effect on antibacterial activity." Applied Clay Science. 2004. pp. 13-19. vol. 27.
Ward, et al., The Journal of TRAUMA Injury, Infection, and Critical Care, Comparison of a New Hemostatic Agent to Current Combat Hemostatic Agents in a Swine Model of Lethal Extremity Arterial Hemorrhage, Aug. 2007, pp. 276-284.

* cited by examiner

DEVICES AND METHODS FOR THE DELIVERY OF BLOOD CLOTTING MATERIALS TO BLEEDING WOUNDS

CROSS REFERENCE TO RELATED APPLICATION

This application is a continuation-in-part application of U.S. patent application Ser. No. 11/054,918, filed Feb. 9, 2005, the contents of which are incorporated herein by reference in their entirety.

TECHNICAL FIELD

The present invention relates generally to blood clotting devices and, more particularly, to blood clotting materials, devices incorporating such materials, and methods for the delivery of such materials for use as bleeding control devices.

BACKGROUND OF THE INVENTION

Blood is a liquid tissue that includes red cells, white cells, corpuscles, and platelets dispersed in a liquid phase. The liquid phase is plasma, which includes acids, lipids, solubilzed electrolytes, and proteins. The proteins are suspended in the liquid phase and can be separated out of the liquid phase by any of a variety of methods such as filtration, centrifugation, electrophoresis, and immunochemical techniques. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can be wounded. Often bleeding is associated with such wounds. In some circumstances, the wound and the bleeding are minor, and normal blood clotting functions in addition to the application of simple first aid are all that is required. Unfortunately, however, in other circumstances substantial bleeding can occur. These situations usually require specialized equipment and materials as well as personnel trained to administer appropriate aid. If such aid is not readily available, excessive blood loss can occur. When bleeding is severe, sometimes the immediate availability of equipment and trained personnel is still insufficient to stanch the flow of blood in a timely manner.

Moreover, severe wounds can often be inflicted in remote areas or in situations, such as on a battlefield, where adequate medical assistance is not immediately available. In these instances, it is important to stop bleeding, even in less severe wounds, long enough to allow the injured person or animal to receive medical attention.

In an effort to address the above-described problems, materials have been developed for controlling excessive bleeding in situations where conventional aid is unavailable or less than optimally effective. Although these materials have been shown to be somewhat successful, they are sometimes not effective enough for traumatic wounds and tend to be expensive. Furthermore, these materials are sometimes ineffective in some situations and can be difficult to apply as well as remove from a wound.

Additionally, or alternatively, the previously developed materials can produce undesirable side effects. For example, prior art blood clotting material is generally a powder or a fine particulate in which the surface area of the material often produces an exothermic reaction upon the application of the material to blood. Oftentimes excess material is unnecessarily poured onto a wound, which can exacerbate the exothermic effects. Depending upon the specific attributes of the material, the resulting exothermia may be sufficient to cause discomfort to or even burn the patient. Although some prior art patents specifically recite the resulting exothermia as being a desirable feature that can provide clotting effects to the wound that are similar to cauterization, there exists the possibility that the tissue at and around the wound site may be undesirably impacted.

Furthermore, to remove such materials from wounds, irrigation of the wound is often required. If an amount of material is administered that causes discomfort or burning, the wound may require immediate flushing. In instances where a wounded person or animal has not yet been transported to a facility capable of providing the needed irrigation, undesirable effects or over-treatment of the wound may result.

Bleeding can also be a problem during surgical procedures. Apart from suturing or stapling an incision or internally bleeding area, bleeding is often controlled using a sponge or other material used to exert pressure against the bleed site and/or absorb the blood. However, when the bleeding becomes excessive, these measures may not be sufficient to stop the flow of blood. Moreover, any highly exothermic bleed-control material may damage the tissue surrounding the bleed site and may not be configured for easy removal after use.

Based on the foregoing, it is a general object of the present invention to provide devices for controlling bleeding and methods of their use that overcome or improve upon the prior art.

SUMMARY OF THE INVENTION

According to one aspect, the present invention resides in an apparatus for promoting the clotting of blood, thereby controlling bleeding. The apparatus comprises a receptacle for retaining a blood clotting material in particulate form therein. At least a portion of the receptacle is defined by a mesh having openings therein such that when the apparatus is applied to a bleed site, the particulate blood clotting material comes into contact with blood through the openings. A zeolite powder is incorporated into the mesh to facilitate the blood clotting qualities when the apparatus is applied to a bleeding wound.

Other aspects of the present invention include a pad for controlling bleeding and a bandage applicable to a bleeding wound. In both the pad and the bandage, there is a mesh structure and particles of blood clotting material retained therein. The mesh structure impregnated with or otherwise includes zeolite powder. In the pad embodiment, there is a rigid or semi-rigid support attached to the mesh structure to facilitate the application of pressure to the pad and the wound. In the bandage, there is a flexible substrate attached to the mesh structure, the substrate being a cloth or plastic member that may be adhesively attached to cover a wound. In any embodiment, the mesh structure may be defined by a plurality of members (strands, filaments, or strips of synthetic or natural material) interconnected and arranged to define openings. The openings are sized to allow contact to be maintained between the particles of the blood clotting material and blood.

An advantage of the present invention is that upon completion of the application of any of the devices of the present invention to a bleeding wound, the devices can be easily removed. In particular, because the blood clotting material is zeolite or oxidized cellulose in granule, bead, or pellet form and encased in a pouch or mesh structure, the material can be cleanly pulled away from the treated wound and disposed of. Accordingly, little or no irrigation of the wound is required to flush away remaining blood clotting material. In devices in which the pouch containing blood clotting material is incorporated into an adhesive bandage, the device can be left on the wound for the amount of time necessary to cause clotting.

Another advantage is that the particlized form of zeolite used as the blood clotting material allows the material to react less exothermically with blood. As the particle size increases (e.g., from fine to coarse), the surface area of the particles that the blood can come into contact with decreases. The porous nature of the zeolite still allows liquid blood constituents to be wicked away to cause thickening of the blood, thereby facilitating the formation of clots. Because the particle surface area exposed to the blood is reduced, a less aggressive drawing of moisture from the blood is realized, which thereby tempers the exothermic effects experienced at the wound site.

With regard to embodiments in which zeolite powder is included in the mesh, one advantage is that the contacting surface area between the powder and the tissue of the wound site is increased. In particular, the flow of blood to the mesh results in immediate clotting effects because a time delay due to the blood having to flow around the mesh material to the blood clotting material is avoided.

Still another advantage of the present invention is that the proper dose of blood clotting material can be readily applied to an open wound. Particularly when the device is a porous pouch containing zeolite or oxidized cellulose, the device can be readily removed from sterilized packaging and held directly at the points from which blood emanates to facilitate clotting of the blood without spilling powder or pellets outside the wound area. Guesswork, estimation, or calculation of the amounts of blood clotting material for application to a bleeding wound is eliminated. Accordingly, little or no blood clotting material is wasted.

DETAILED DESCRIPTION OF THE PREFERRED EMBODIMENTS

Disclosed herein are devices and methods for delivering materials to wounds to promote the clotting of blood and the dressing of the wounds. The devices generally comprise expedients or apparatuses that can be applied to bleeding wounds such that the materials contact the tissue of the wound to minimize or stop blood flow of blood by absorbing at least portions of the liquid phases of the blood, thereby promoting clotting. One apparatus comprises a receptacle for retaining molecular sieve material in particulate form or oxidized cellulose material in particulate form therein. At least a portion of the receptacle is defined by a mesh having openings therein, and at least a portion of the particulate molecular sieve material or oxidized cellulose material is in direct contact with blood through the openings. As used herein, the terms "particle" and "particulate" are intended to refer to balls, beads, pellets, rods, granules, polymorphous shapes, and combinations of the foregoing.

In embodiments incorporating a molecular sieve material as the blood clotting material, the molecular sieve material used in the present invention may be a synthetic polymer gel, cellulosic material, porous silica gel, porous glass, alumina, hydroxyapatite, calcium silicate, zirconia, zeolite, or the like. Exemplary synthetic polymers include, but are not limited to, stylene-divinylbenzene copolymer, cross-linked polyvinyl alcohol, cross-linked polyacrylate, cross-linked vinyl ether-maleic anhydride copolymer, cross-linked stylene-maleic anhydride copolymer or cross-linked polyamide, and combinations thereof.

The molecular sieve material is preferably a zeolite. Other molecular sieve materials that may be used include, but are not limited to, faujasite. As used herein, the term "zeolite" refers to a crystalline form of aluminosilicate having the ability to be dehydrated without experiencing significant changes in the crystalline structure. The zeolite may include one or more ionic species such as, for example, calcium and sodium moieties. Typically, the zeolite is a friable material that is about 90% by weight calcium and about 10% by weight sodium. The calcium portion contains crystals that are about 5 angstroms in size, and the sodium portion contains crystals that are about 4 angstroms in size. The preferred molecular structure of the zeolite is an "A-type" crystal, namely, one having a cubic crystalline structure that defines round or substantially round openings.

The zeolite may be mixed with or otherwise used in conjunction with other materials having the ability to be dehydrated without significant changes in crystalline structure. Such materials include, but are not limited to, magnesium sulfate, sodium metaphosphate, calcium chloride, dextrin, a polysaccharide, combinations of the foregoing materials, and hydrates of the foregoing materials.

Zeolites for use in the disclosed applications may be naturally occurring or synthetically produced. Numerous varieties of naturally occurring zeolites are found as deposits in sedimentary environments as well as in other places. Naturally occurring zeolites that may be applicable to the compositions described herein include, but are not limited to, analcite, chabazite, heulandite, natrolite, stilbite, and thomosonite. Synthetically produced zeolites that may also find use in the compositions and methods described herein are generally produced by processes in which rare earth oxides are substituted by silicates, alumina, or alumina in combination with alkali or alkaline earth metal oxides.

Various materials may be mixed with, associated with, or incorporated into the zeolites to maintain an antiseptic environment at the wound site or to provide functions that are supplemental to the clotting functions of the zeolites. Exemplary materials that can be used include, but are not limited to, pharmaceutically-active compositions such as antibiotics, antifungal agents, antimicrobial agents, anti-inflammatory agents, analgesics (e.g., cimetidine, chlorpheniramine maleate, diphenhydramine hydrochloride, and promethazine hydrochloride), bacteriostatics, compounds containing silver ions, and the like. Other materials that can be incorporated to provide additional hemostatic functions include ascorbic acid, tranexamic acid, rutin, and thrombin. Botanical agents having desirable effects on the wound site may also be added.

In embodiments incorporating oxidized cellulose as the blood clotting material, the oxidized cellulose used in the present invention is a chemically oxidized form of a common cellulose fiber such as cotton and is also known as cellulosic acid, absorbable cellulose, or polyanhydroglucuronic acid. The degree of oxidation of the fiber is a function of the carboxylation content of the fibrous cellulose material. In particular, as the number of carboxyl groups on the cellulose structure is increased, the oxidation content correspondingly increases. Oxidized cellulose may be manufactured by the action of nitrogen dioxide gas ($NO_2$) on cellulose fiber. Other methods of manufacturing oxidized cellulose include oxidation of cellulose fiber with aqueous oxidizing agents such as hypochlorite salts, although the use of such agents is less preferred than the use of nitrogen dioxide gas.

Figure 1:
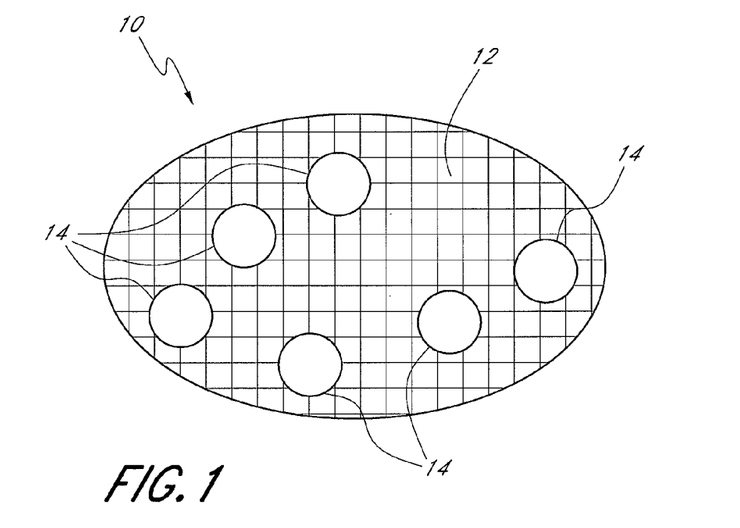
FIG. 1 is a schematic representation of a blood clotting device of the present invention.

In one embodiment of the present invention, a device for facilitating the clotting of blood directly at a wound site is shown with reference to FIG. 1. The device is a permeable pouch that allows liquid to enter to contact blood clotting zeolite (or other molecular sieve material) or oxidized cellulose material retained therein. Although the devices of the present invention are described hereinafter as including zeolite as the blood clotting agent, it should be understood that the blood clotting agent may be oxidized cellulose. Sealed packaging (not shown) provides a sterile environment for storing the device until it can be used. The device, which is shown generally at 10 and is hereinafter referred to as "pouch 10," comprises a screen or mesh 12 and zeolite particles 14 retained therein by the screen or mesh. The mesh 12 is closed on all sides and defines openings that are capable of retaining the zeolite particles 14 therein while allowing liquid to flow through. As illustrated, the mesh 12 is shown as being flattened out, and only a few zeolite particles 14 are shown.

The zeolite particles 14 are substantially spherical or irregular in shape (e.g., balls, beads, pellets, or the like) and about 0.2 millimeters (mm) to about 10 mm in diameter, preferably about 1 mm to about 7 mm in diameter, and more preferably about 2 mm to about 5 mm in diameter. In any embodiment (balls, beads, pellets, etc.), less particle surface area is available to be contacted by blood as the particle size is increased. Therefore, the rate of clotting can be controlled by varying the particle size. Furthermore, the adsorption of moisture (which also has an effect on the exothermic effects of the zeolite) can also be controlled.

The mesh 12 is defined by interconnected strands, filaments, or strips of material. The strands, filaments, or strips can be interconnected in any one or a combination of manners including, but not limited to, being woven into a gauze, intertwined, integrally-formed, and the like. Preferably, the interconnection is such that the mesh can flex while substantially maintaining the dimensions of the openings defined thereby. The material from which the strands, filaments or strips are fabricated may be a polymer (e.g., nylon, polyethylene, polypropylene, polyester, or the like), metal, fiberglass, or an organic substance (e.g., cotton, wool, silk, or the like).

Figure 2:
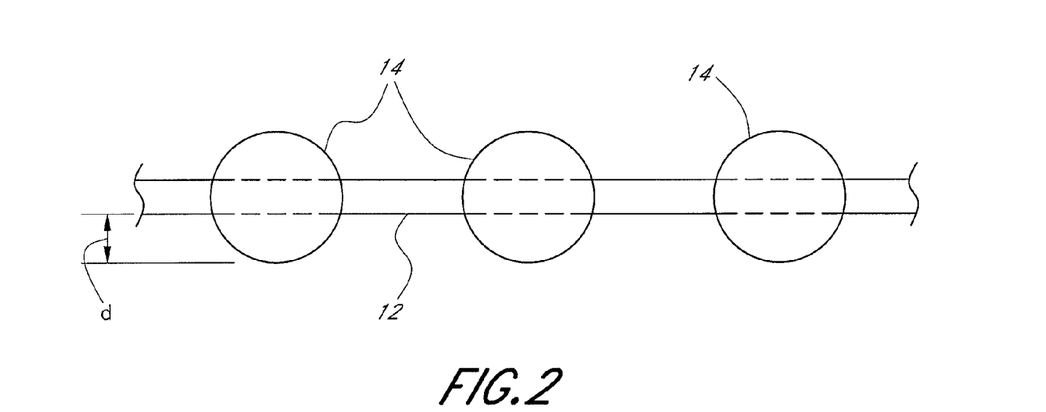
FIG. 2 is a side view of the blood clotting device of FIG. 1 illustrating the retaining of blood clotting particles in a mesh container.

Referring now to FIG. 2, the openings defined by the mesh 12 are dimensioned to retain the zeolite particles 14 but to accommodate the flow of blood therethrough. Because the mesh 12 may be pulled tight around the zeolite particles 14, the particles may extend through the openings by a distance d. If the zeolite particles 14 extend through the openings, the particles are able to directly contact tissue to which the pouch 10 is applied. Thus, blood emanating from the tissue immediately contacts the zeolite particles 14, and the water phase thereof is wicked into the zeolite material, thereby facilitating the clotting of the blood. However, it is not a requirement of the present invention that the zeolite particles protrude through the mesh.

To apply the pouch 10 to a bleeding wound, the pouch is removed from the packaging and placed on the bleeding wound. The zeolite particles 14 in the mesh 12 contact the tissue of the wound and/or the blood, and at least a portion of the liquid phase of the blood is adsorbed by the zeolite material, thereby promoting the clotting of the blood.

Figure 3:
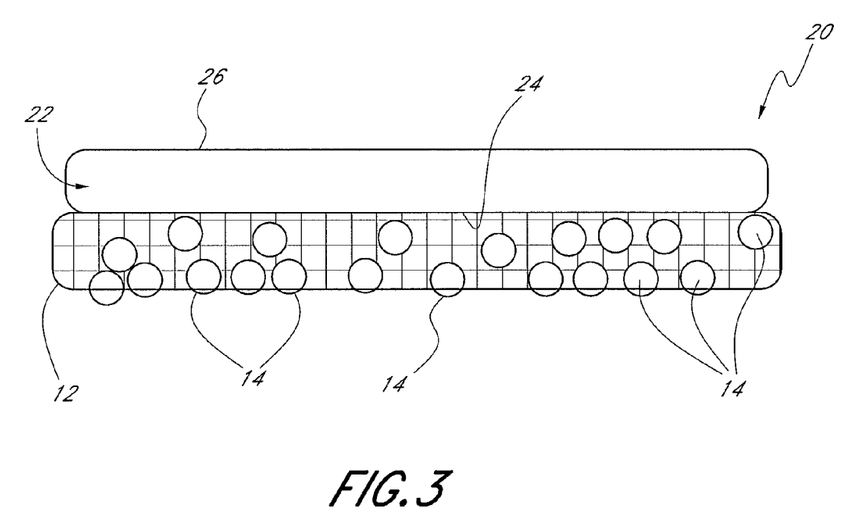
FIG. 3 is a side view of a pressure pad incorporating the blood clotting particles encapsulated in a mesh container for pressure application to a bleeding wound.

Another embodiment of the present invention is a pad which is shown at 20 with reference to FIG. 3 and is hereinafter referred to as "pad 20." The pad 20 comprises the mesh 12, zeolite (or other molecular sieve) particles 14 (or oxidized cellulose particles) retained therein by the mesh 12, and a support 22 to which pressure may be applied in the application of the pad 20 to a bleeding wound. The mesh 12, as above, has openings that are capable of retaining the zeolite particles 14 therein while allowing the flow of blood therethrough.

The mesh 12 is stitched, glued, clamped, or otherwise mounted to the support 22. The support 22 comprises an undersurface 24 against which the zeolite particles 14 are held by the container 12 and a top surface 26. The undersurface 24 is impermeable to the zeolite particles 14 (migration of the particles into the support 22 is prevented) and is further resistant to the absorption of water or other fluids. The top surface 26 is capable of having a pressure exerted thereon by a person applying the pad 20 to a bleeding wound or by a weight supported on the top surface 26. The entire support 22 is rigid or semi-rigid so as to allow the application of pressure while minimizing discomfort to the patient.

To apply the pad 20 to a bleeding wound, the pad 20 is removed from its packaging and placed on the bleeding wound. As with the pouch of the embodiment of FIGS. 1 and 2, the zeolite particles 14 are either in direct contact with the tissue of the wound or are in direct contact with the blood. Pressure may be applied to the wound by pressing on the top surface 26 with a hand or by placing a weight on the surface, thereby facilitating the contact between the zeolite particles 14 and the wound and promoting the adsorption of the liquid phase of the blood. The pad 20 (with or without a weight) may also be held onto the wound using a strapping device such as a belt, an elastic device, hook-and-loop material, combinations of the foregoing devices and materials, and the like.

Figure 4:
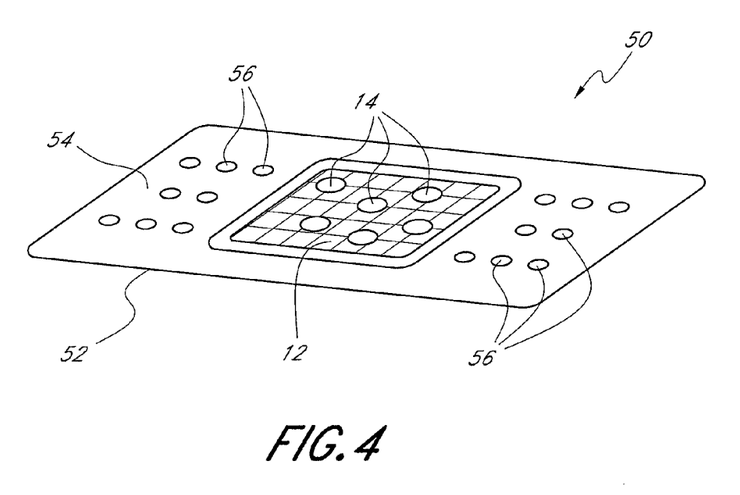
FIG. 4 is a perspective view of a bandage incorporating the blood clotting particles in a mesh container for application to a bleeding wound.

Referring now to FIG. 4, another embodiment of the present invention is a bandage, shown at 50, which comprises zeolite particles 14 (or some other molecular sieve material or oxidized cellulose in particle form) retained in a mesh 12 and mounted to a flexible substrate 52 that can be applied to a wound (for example, using a pressure-sensitive adhesive to adhere the bandage 50 to the skin of a wearer). The mesh 12 is stitched, glued, or otherwise mounted to a substrate 52 to form the bandage 50.

The substrate 52 is a plastic or a cloth member that is conducive to being retained on the skin of an injured person or animal on or proximate a bleeding wound. An adhesive 54 is disposed on a surface of the substrate 52 that engages the skin of the injured person or animal. Particularly if the substrate 52 is a non-breathable plastic material, the substrate may include holes 56 to allow for the dissipation of moisture evaporating from the skin surface.

Figure 5:
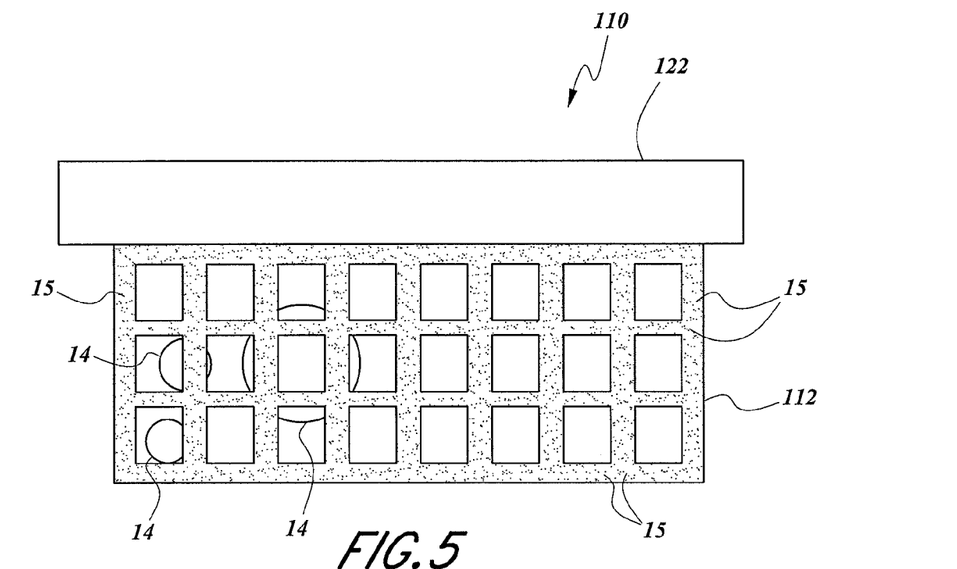
FIG. 5 is a side view of a blood clotting device incorporating blood clotting particles retained in a mesh impregnated with zeolite particles.

Referring now to FIG. 5, another embodiment of the present invention comprises a device 110 having the zeolite particles 14 (or other blood clotting material such as oxidized cellulose) as described above retained within a fabric pouch. The fabric pouch is a zeolite-impregnated mesh 112 having hemostatic qualities, namely, the hemostatic properties of zeolite. The device 110 may include a support 122, thereby defining a pad. When the device 110 is a pad, the support 122 provides a surface at which pressure may be applied in the application of the device to a bleeding wound. Without the support 122, the device 110 may be used as a surgical sponge.

The zeolite-laden mesh 112 is defined by interconnected strands, filaments, or strips of material that are interconnected by being woven, intertwined, or integrally formed as in the above-disclosed embodiments. The mesh 112 includes particles of zeolite powder 15. Although the particles of zeolite powder 15 are shown as being concentrated along portions of the edges of the mesh 112, it should be understood that the zeolite powder is dispersed throughout the material from which the mesh is fabricated. Preferably, the interconnection of the strands, filaments, or strips to form the mesh 112 is such that the device 110 can flex while substantially maintaining the dimensions of the openings, thereby allowing the zeolite particles 14 to be retained.

Figure 6:
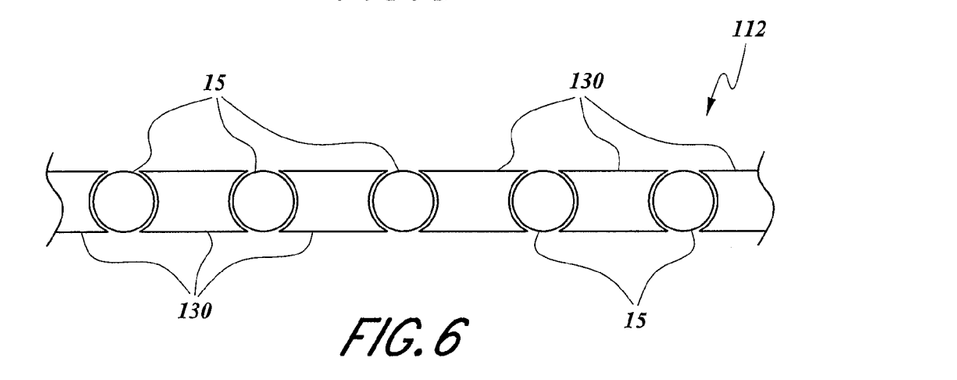
FIG. 6 is a side view of one embodiment of the mesh of the device of FIG. 5.
Figure 7:
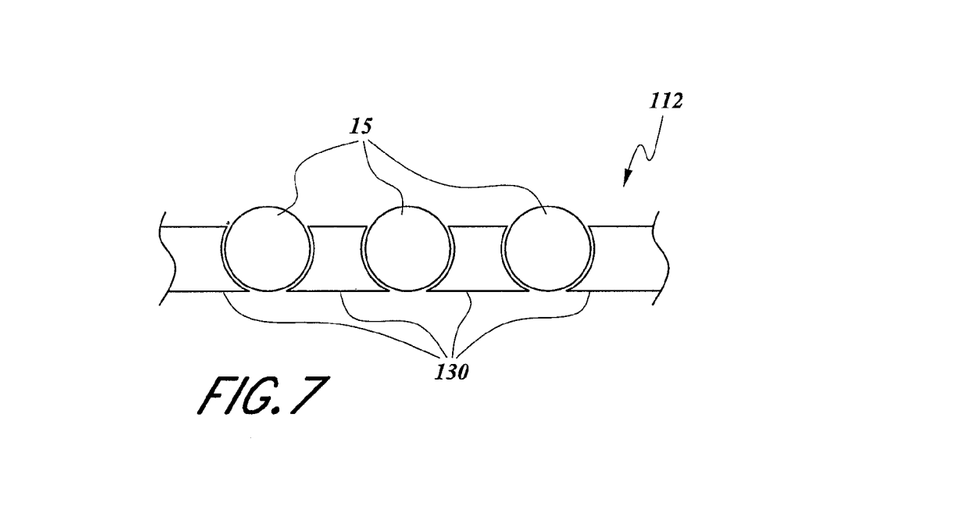
FIG. 7 is a side view of another embodiment of the mesh of the device of FIG. 5.

Referring now to FIGS. 6 and 7, zeolite is impregnated into or otherwise retained by the material of the strands, filaments, or strips that define the mesh 112. In particular, the particles of zeolite powder 15 may be captured within a matrix material 130 such that the particles contact the bleeding tissue when the strands, filaments, or strips defining the mesh 112 are brought into contact with the wound. The present invention is not limited to zeolite impregnated or incorporated into the material of the mesh, however, as other materials such as oxidized cellulose may be impregnated or incorporated into the mesh material. As is shown in FIG. 6, the zeolite powder 15 may be captured and held within the outer surface of the matrix material 130. In such an embodiment, the matrix material 130 is preferably sufficiently porous to facilitate the flow of blood therethrough, thus allowing liquid phases of the blood to be at least partially absorbed by the zeolite powder 15 prior to contacting the zeolite particles (or other molecular sieve materials) retained in the mesh 112. As is shown in FIG. 7, the zeolite powder may be captured so as to protrude above the surface of the matrix material 130.

Figure 8:
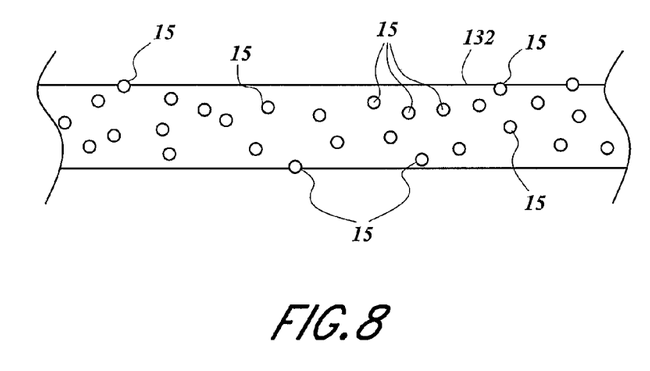
FIG. 8 is a side view of another embodiment of the mesh of the device of FIG. 5.

Referring to FIG. 8, the zeolite powder 15 may be impregnated into a substrate material 132 and retained therein by any suitable method. In the impregnation of the zeolite powder 15 into the substrate material 132, the substrate material is generally sufficiently soft (e.g., fluid when exposed to heat) to allow for its deformation to accommodate the zeolite powder. The zeolite powder 15 may be impregnated completely into the substrate material 132, or it may be partially impregnated so as to extend out of the substrate material.

In either the embodiment of FIGS. 6 and 7 or of FIG. 8, the matrix material or the substrate material may be a polymer (e.g., nylon, polyethylene, polypropylene, polyester, or the like), metal, fiberglass, or an organic substance (e.g., cotton, wool, silk, or the like). The matrix material or the substrate material may also be cellulose or a cellulose derivative.

Figure 9:
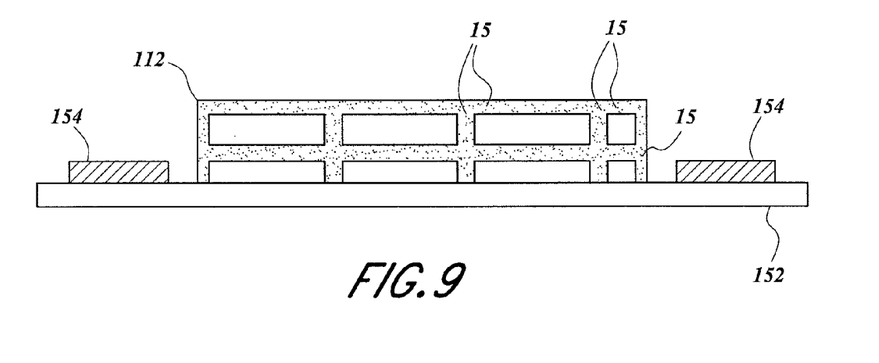
FIG. 9 is a side view of a bandage incorporating blood clotting particles retained in a zeolite-impregnated mesh material.

The zeolite-laden mesh 112 may be utilized in conjunction with a bandage, as is shown in FIG. 9. The mesh 112 (which comprises the zeolite powder 15) may be mounted to a flexible substrate 152 that can be applied to a wound in a manner similar to that described above with reference to FIG. 4. The mesh 112 may be stitched, glued, or otherwise mounted to the substrate 152, which may be a plastic or cloth member that is retained on the skin of an injured person or animal on or proximate the bleeding wound (e.g., via an adhesive 154).

In the preparation of zeolite material for the devices of the present invention (i.e., formation of the material into particle form), an initial level of hydration of the zeolite may be controlled by the application of heat to the zeolite material either before or after the material is formed into particles. However, it has also surprisingly been found that as the particle size of the zeolite is increased, the moisture content has less of a correlative effect on any exothermia produced as the result of mixing the particlized zeolite in blood. As such, formation of the zeolite material into the zeolite particles (shown at 14 in FIGS. 1-4), may be by extrusion, milling, casting, or the like.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. An apparatus for promoting the clotting of blood, comprising: a pouch closed on all sides, defined by a mesh on all sides, and a first blood clotting material in powder form incorporated into a material defining said mesh and captured therein so that at least a portion of said powder is exposed on an outer surface defined by said material; and
   a second blood clotting material in loose particulate form retained in said pouch;
   wherein the material defining the mesh comprises openings which are sufficiently large to allow at least a portion of the particulate blood clotting material to extend through the openings to allow contact with blood outside of the pouch.

2. The apparatus for promoting the clotting of blood of claim 1, wherein said first blood clotting material comprises a zeolite.

3. The apparatus for promoting the clotting of blood of claim 2, wherein said second blood clotting material comprises a zeolite.

4. The apparatus for promoting the clotting of blood of claim 3, wherein the second blood clotting material in loose particulate form comprises zeolite particles having diameters of about 0.2 mm to about 10 mm.

5. The apparatus for promoting the clotting of blood of claim 3, wherein the second blood clotting material in loose particulate form comprises zeolite particles having diameters of about 1 mm to about 7 mm.

6. The apparatus for promoting the clotting of blood of claim 3, wherein the second blood clotting material in loose particulate form comprises zeolite particles having diameters of about 2 mm to about 5 mm.

7. The apparatus for promoting the clotting of blood of claim 1, wherein said mesh structure is flexible.

8. The apparatus for promoting the clotting of blood of claim 1, wherein at least a portion of said material of said mesh defines a matrix in which said first blood clotting material in powder form is captured.

9. The apparatus for promoting the clotting of blood of claim 1, wherein at least a portion of said material of said mesh is impregnated with said first blood clotting material in powder form.

10. The apparatus for promoting the clotting of blood of claim 1, wherein the material defining the mesh comprises at least one of: polymers, metals, fiberglass, organic substances, and cellulose.

11. The apparatus for promoting the clotting of blood of claim 1, wherein said second blood clotting material comprises oxidized cellulose.

12. The apparatus for promoting the clotting of blood of claim 1, further comprising a support attached to a portion of the mesh defining said pouch.

13. The apparatus for promoting the clotting of blood of claim 3, further comprising a support attached to a portion of the mesh defining said pouch.

14. The apparatus for promoting the clotting of blood of claim 4, further comprising a support attached to a portion of the mesh defining said pouch.

15. The apparatus for promoting the clotting of blood of claim 5, further comprising a support attached to a portion of the mesh defining said pouch.

16. The apparatus for promoting the clotting of blood of claim 6, further comprising a support attached to a portion of the mesh defining said pouch.

17. The apparatus for promoting the clotting of blood of claim 11, further comprising a support attached to a portion of the mesh defining said pouch.

18. The apparatus for promoting the clotting of blood of claim 1, further comprising a substrate for affixing the pouch to a bleeding area.

19. The apparatus for promoting the clotting of blood of claim 1, further comprising an adhesive on said substrate, said adhesive being configured to facilitate affixing the pouch on the skin of a wearer.

20. The apparatus for promoting the clotting of blood of claim 3, further comprising a substrate for affixing the pouch to a bleeding area.

* * * * *